(12) United States Patent
Gangadhar et al.

(10) Patent No.: US 9,000,224 B1
(45) Date of Patent: Apr. 7, 2015

(54) PROCESS FOR THE PREPARATION OF PILLAR[5]QUINONE

(71) Applicant: Council of Scientific & Industrial Research, New Delhi (IN)

(72) Inventors: Jessy Sanjayan Gangadhar, Pune (IN); Ishwara Shivakumar Kilingaru, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/445,471

(22) Filed: Jul. 29, 2014

(30) Foreign Application Priority Data

Jul. 29, 2013 (IN) ............................ 2243/DEL/2103

(51) Int. Cl.
*C07C 45/00* (2006.01)
*C07C 46/02* (2006.01)
(52) U.S. Cl.
CPC ...................................... *C07C 46/02* (2013.01)

(58) Field of Classification Search
CPC .... C07C 45/513; C07C 46/02; C07C 2101/18
USPC .................................................. 568/361, 367
See application file for complete search history.

(56) References Cited

PUBLICATIONS

Derong Cao et al., "A Facile and Efficient Preparation of Fillararenes and a Pillarquinone**," Angew. Chem. Int. Ed., 2009, vol. 48, 9721-9723.
Ka-Un Lao et al., "A Computational Study of Unique Properties of Pillar[n]quinones: Self-Assembly to Tubular Structures and Potential Applications as Electron Acceptors and Anion Recognizers," Journal of Computational Chemistry, vol. 32, No. 12, 2716-2726 (2010).

*Primary Examiner* — Sikarl Witherspoon
(74) *Attorney, Agent, or Firm* — Abelman, Frayne & Schwab

(57) ABSTRACT

The present invention relates to a process for the preparation of pillar[5]quinone and further relates to an easy-to-operate and chromatography-free process for the preparation of crystalline pillar[5]quinone by the oxone/iodobenzene-mediated oxidative de-aromatization of readily available 1,4-dimethoxypillar[5]arenes in good yields.

5 Claims, 14 Drawing Sheets

PROCESS FOR THE PREPARATION OF PILLAR[5]QUINONE

FIELD OF THE INVENTION

The present invention relates to a process for the preparation of pillar[5]quinone. More particularly, the present invention relates to crystalline form of pillar[5]quinone and an easy-to-operate, chromatography-free process for the preparation of crystalline pillar[5]quinone from 1,4-dimethoxypillar[5]arenes.

BACKGROUND OF THE INVENTION

Pillar[5]arenes, a new class of fascinating cyclophanes, continue to attract the attention of chemists and the interest in this class of macrocycles continues unabated primarily due to their enormous application potential in diverse areas. The most notable feature of pillar[5]arenes is their deep π-encircled internal cavity capable of accommodating guest molecules through diverse non-covalent interactions, thereby raising the hope of developing molecular sensors. It is noteworthy that by virtue of their structural architecture, cycloquinones decorated with deep internal cavity essential for molecular sensing, are also being increasingly explored for the development of molecular sensors featuring redox active properties.

A recently reported quinone-based, redox-active resorcin[4]arene cavitand is one such candidate which is able to form kinetically stable host-guest complexes whose binding strength can be modulated by changing the redox state of the cavitand. However, the quinone rings in the aforesaid system do not form part of the cyclamer backbone. Pillar[5]quinone is structurally unique in this respect not only because of the fact that all the five quinone rings are part of the cyclamer backbone, but also due to the symmetrical crowning of the periphery by ten carbonyl oxygen atoms.

Article Titled "A computational study of unique properties of pillar[n]quinones: self-assembly to tubular structures and potential applications as electron acceptors and anion recognizers" by Lao K U et al. publishes in *J Comput Chem.* 2011, 32(12), 2716-26 reports computational studies that have suggested that pillar[5]quinone could showcase intramolecular charge transfer upon excitation of electrons from HOMO to LUMO, owing to the large difference in the electron distribution between them. Furthermore, pillar[5]quinone-derived systems have been predicted to be promising candidates for trapping anionic halogens. Computational models employed to study pillar[5]quinone predicted these compounds to be an efficient electron acceptor. Also, the theoretical studies anticipated that pillar[5]quinone can efficiently trap anions by CH-π interactions. Bromide and chloride can fit inside the pillar[5]quinone. Computational studies also foresaw the possibility of supramolecular tubular aggregation of monomeric pillar[5]quinone by CH—O interactions.

Article Titled "A Facile and Efficient Preparation of Pillararenes and a Pillarquinone" by Derong Cao et al. published in Angewandte Chemie International Edition, 2009, 48 (51), 9721-9723 reports a facile and efficient preparation of pillararenes and a pillarquinone as shown below:

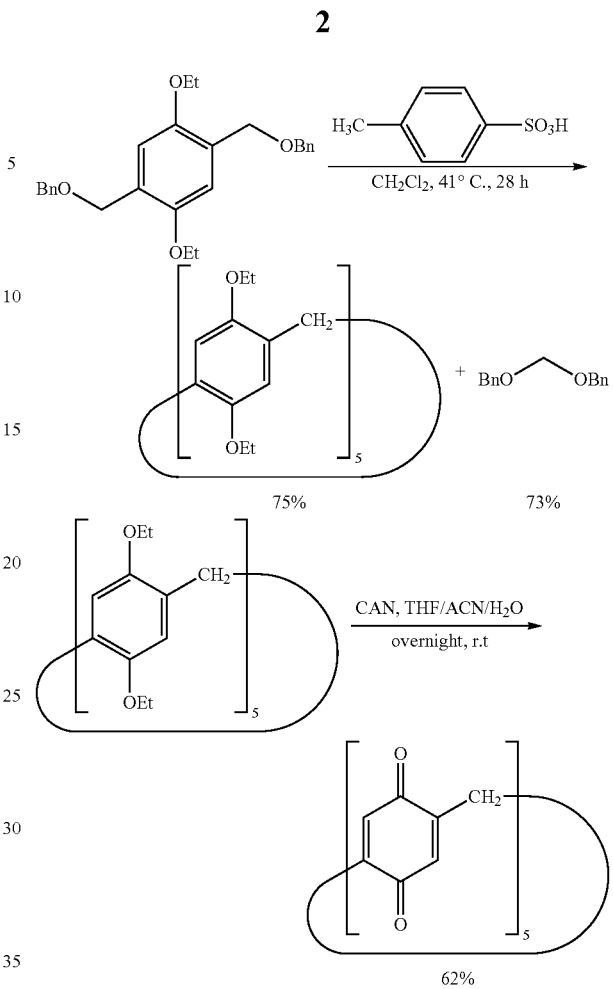

The above process for the synthesis of pillar[5]quinone uses eerie ammonium nitrate (CAN) as an oxidant and the presence of heavy metal in CAN is environmentally hazardous also one of the reactants viz. 2,5-bis(benzyloxymethyl)-1,4-diethoxybenzene is not commercially available and hence it has to be synthesized. Pillar[5]quinone a red colored molecule is isolated by soxhlet extraction using DCM, owing to its poor solubility.

However, the present invention provides an easy-to-operate, chromatography-free, economically and industrially feasible process for the preparation of pillar[5]quinone in multi-gram quantities by the oxone/iodobenzene-mediated oxidative de-aromatization of readily available 1,4-dimethoxypillar[5]arenes in good yields with less hazardous chemicals.

OBJECT OF THE INVENTION

The main object of the present invention is to provide a process for the preparation of pillar[5]quinone.

Another object of the present invention is to provide an efficient, simple and cheap process for the preparation of crystalline form of pillar[5]quinine, optionally containing TCE in good yields.

SUMMARY OF THE INVENTION

An embodiment of the present invention provides a process for the preparation of crystalline form of pillar[5]quinone, wherein the process comprises the following steps:

(a) mixing 1,4-dimethoxypillar[5]arene, acetonitrile, and an oxidizing agent in water to obtain a reaction mixture;
(b) adding iodobenzene to the reaction mixture of step (a) in a mole ratio of 1:2 to obtain a solution; and
(c) stirring the solution of step (b) for a time duration in the range of 45-48 hrs at a temperature in the range of 25-35° C. followed by purification with a solvent to obtain crystalline form of pillar[5]quinone.

In another embodiment of the present invention, the oxidizing agent in step (a) is $2KHSO_5.KHSO_4.K_2SO_4$ (oxone).

In yet another embodiment of the present invention, the solvent used for purification in step (c) is 1,1,2,2,-tetrachloroethane.

In still another embodiment of the present invention, the mole ratio of 1,4-dimethoxypillar[5]arene and oxidizing agent in step (a) is 1:12.

Another embodiment of the present invention provides a process for the preparation of crystalline form of pillar[5] quinine, wherein yield of pillar[5]quinone is in the range of 32% to 34%.

BRIEF DESCRIPTION OF ACCOMPANYING DRAWINGS

Figure 1:
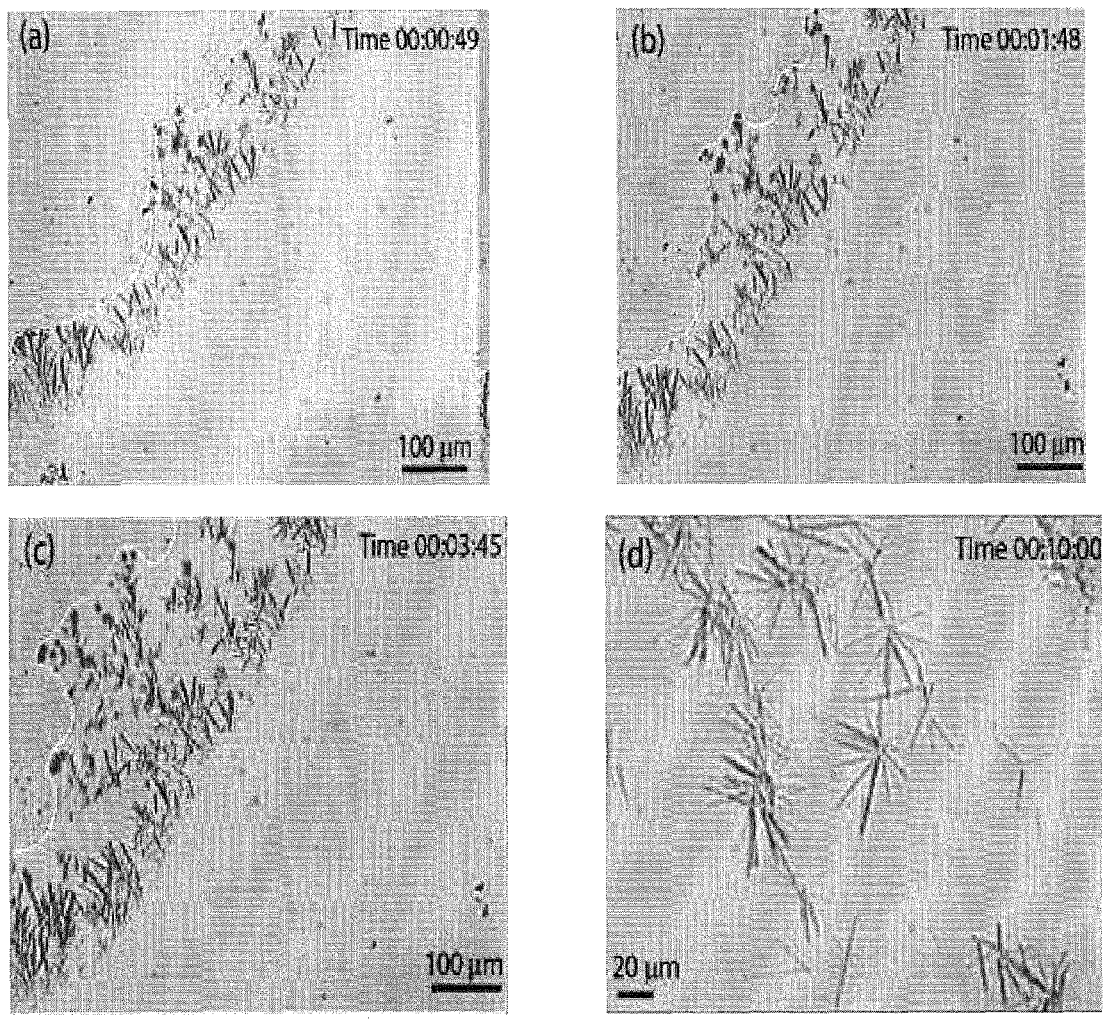
FIG. 1a depicts the polarizing optical microscopy image captured on time-scale showcasing the growth of self-assembly of pillar[5]quinone in 1,1,2,2-tetrachloroethane.
FIG. 1b, FIG. 1c, and FIG. 1d all show additional images of this.
Figure 2:
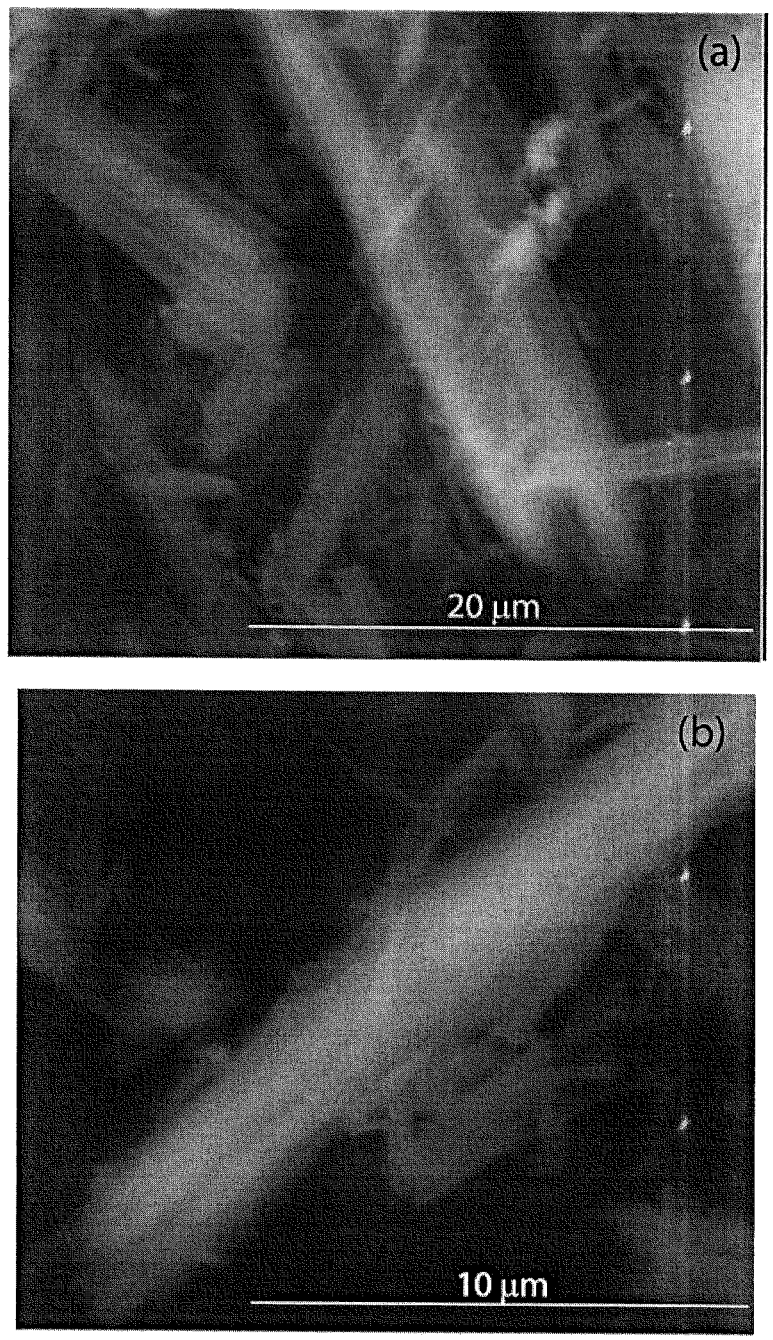
FIGS. 2a and 2b depict the representative SEM images of Pillar[5]quinone devoid of TCE.
Figure 3:
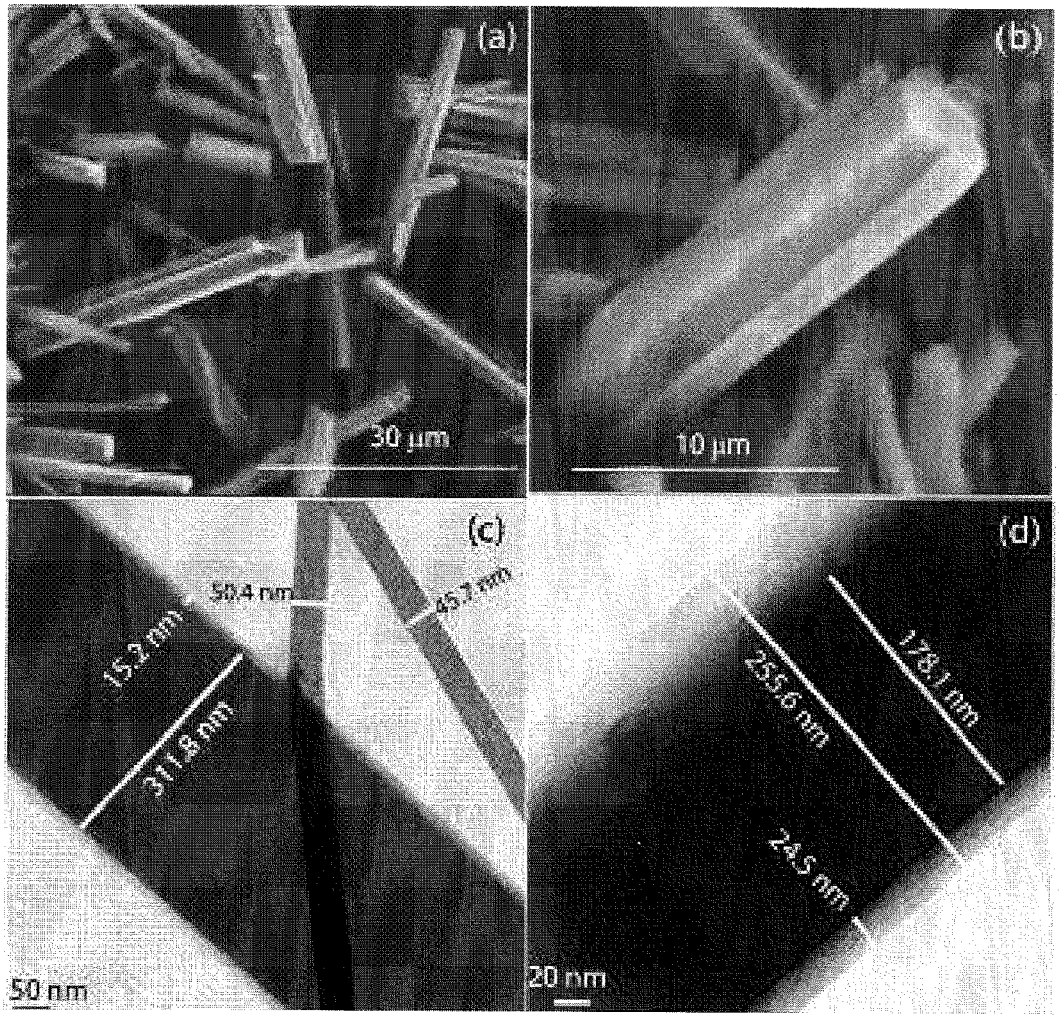
Figure 4A:
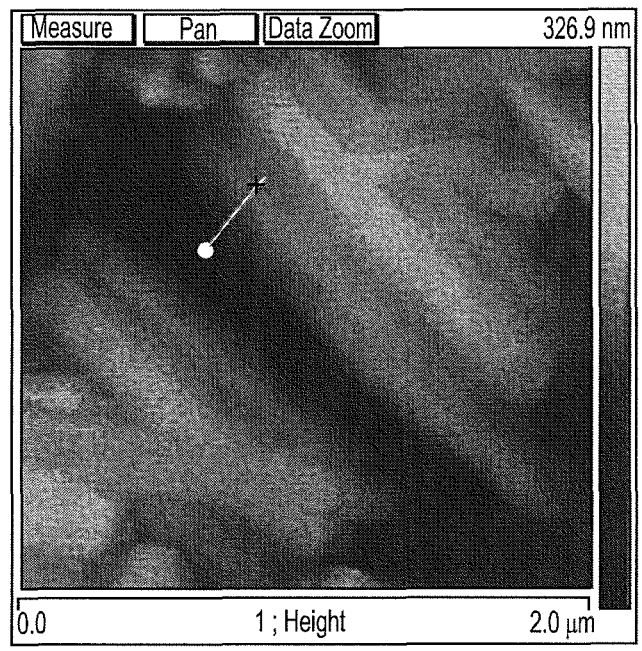
Figure 4A:
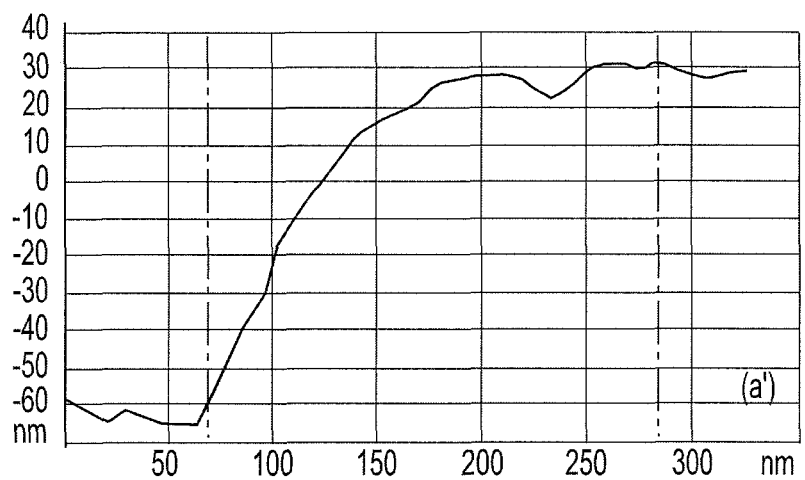
Figure 4B:
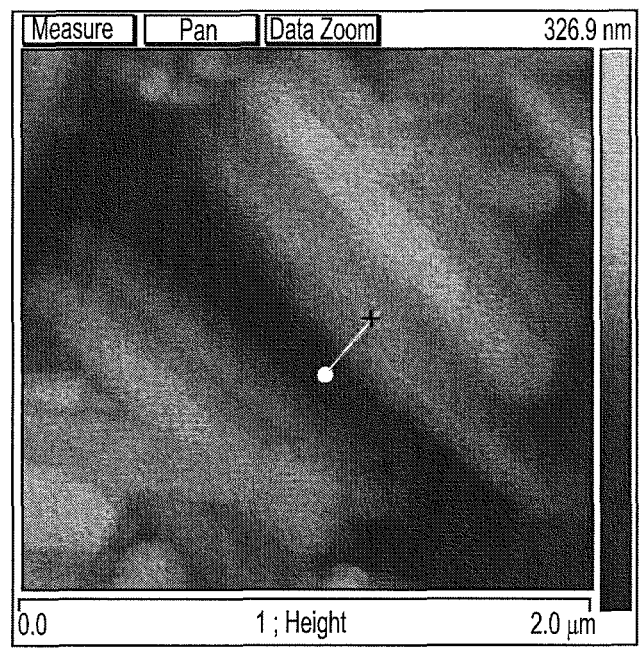
Figure 4B:
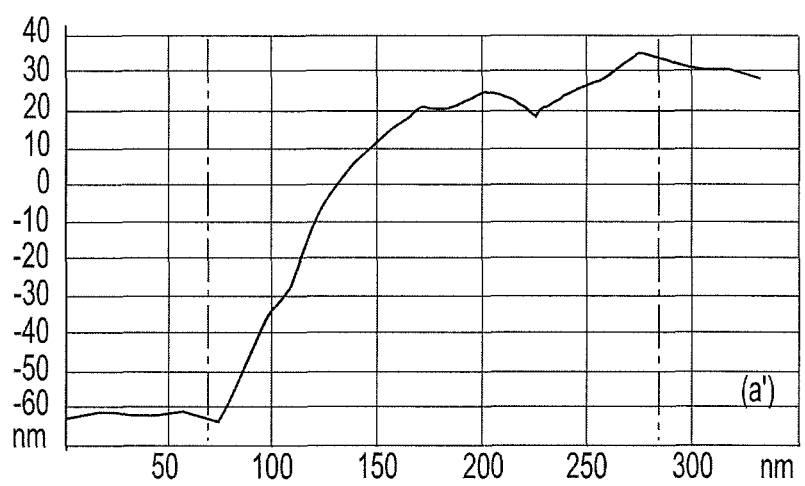
Figure 4C:
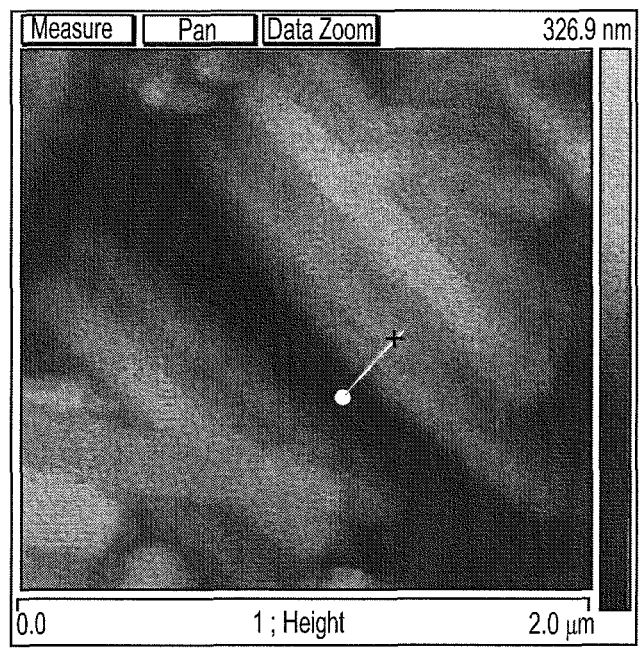
Figure 4C:
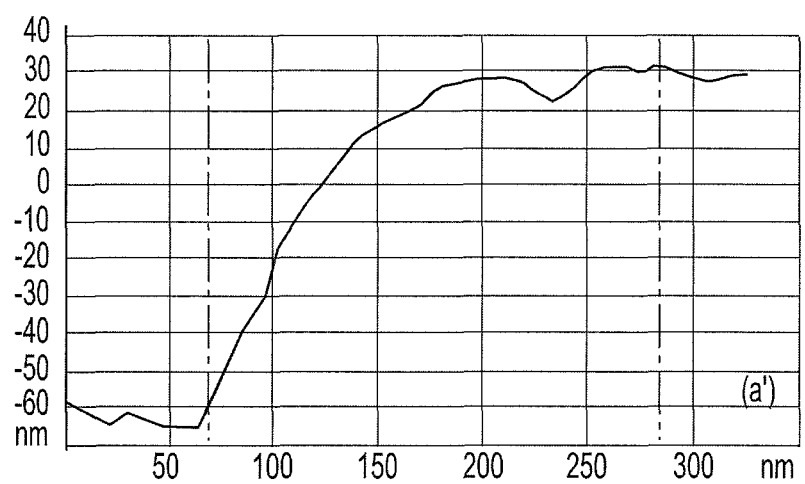

FIGS. 3a, 3b, 3c, and 3d each depict a representative electron microscopy image of P[5]Q-TCE. FIGS. 3a and 3b are SEM images, and FIGS. 3c and 3d are TEM images FIGS. 4a, 4b, and 4c each show a representative TM-AFM height image of P[5]Q-TCE on silicon substrate prepared by disposal into chloroform. These figures are each accompanied by corresponding cross sectional analysis at their right. FIGS. $4a^1$, $4b^1$, and $4c^1$ each denote section analysis along the white line (x-x) in their corresponding height images.

Figure 5A:
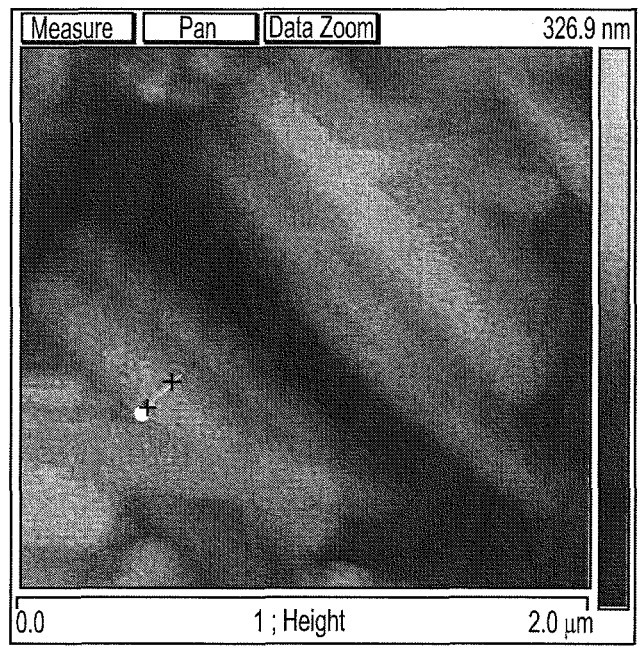
Figure 5B:
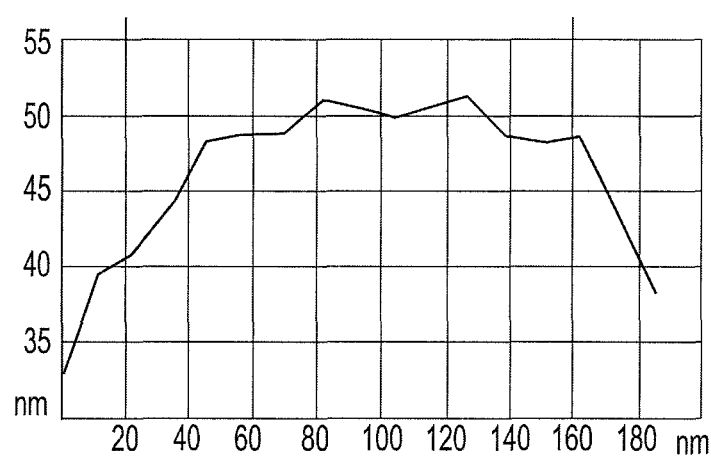

FIGS. 5a and 5b show, respectively, topography of rod-like structures obtained from the TM-AFM height image on silicon substrate, while FIG. 5b shows cross-sectional analysis and the convex curvature of the rod.

Figure 6:
Figure 6:
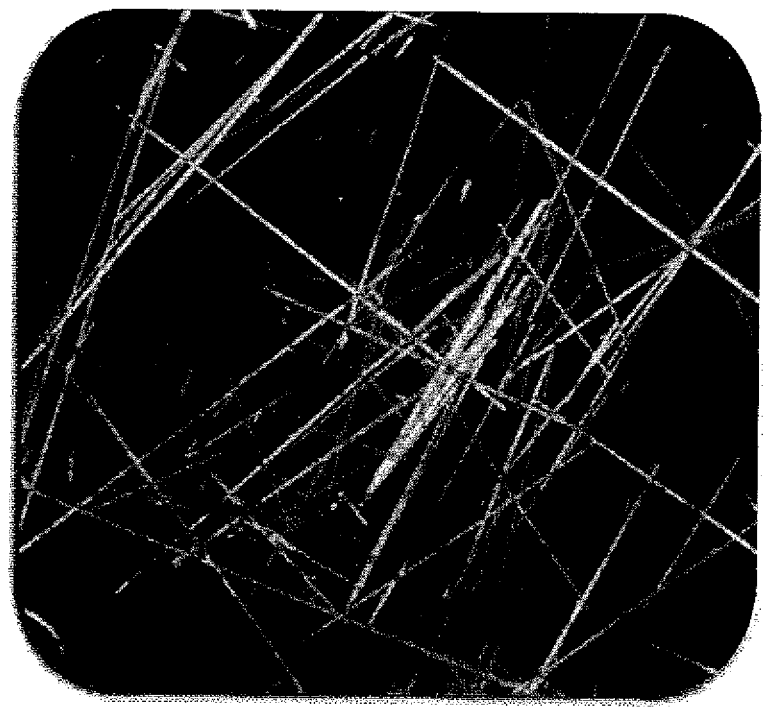

FIGS. 6a and 6b show, respectively, freshly crystallized P[5]Q from 1,1,2,2-tetrachloroethane (6a) and its stereo microscope image (6b).

Figure 7:
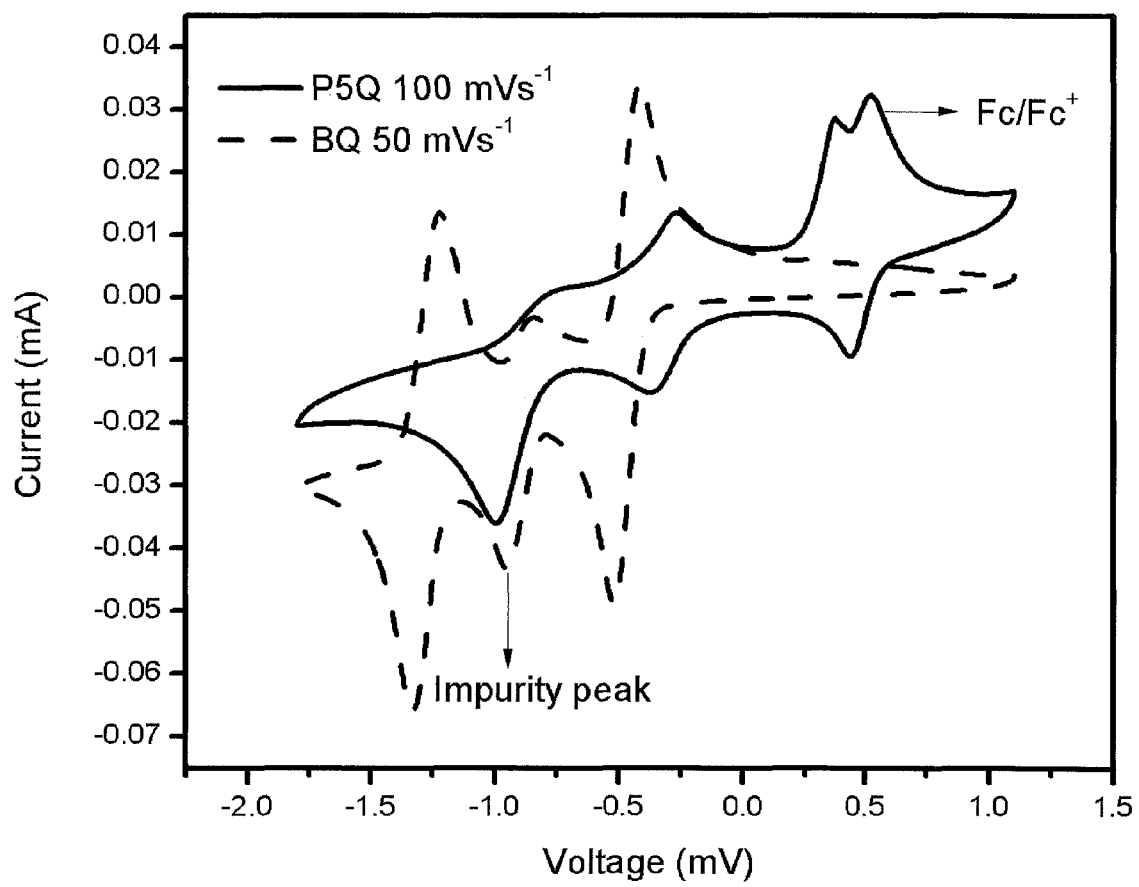

FIG. 7 depicts the cyclic voltammograms of 0.5 mM P[5]Q and 0.25 mM Benzoquinone (BQ) in dried DMF and bottle grade DMF respectively with 0.1 M $TBAPF_6$ as supporting electrolyte.

Figure 8:
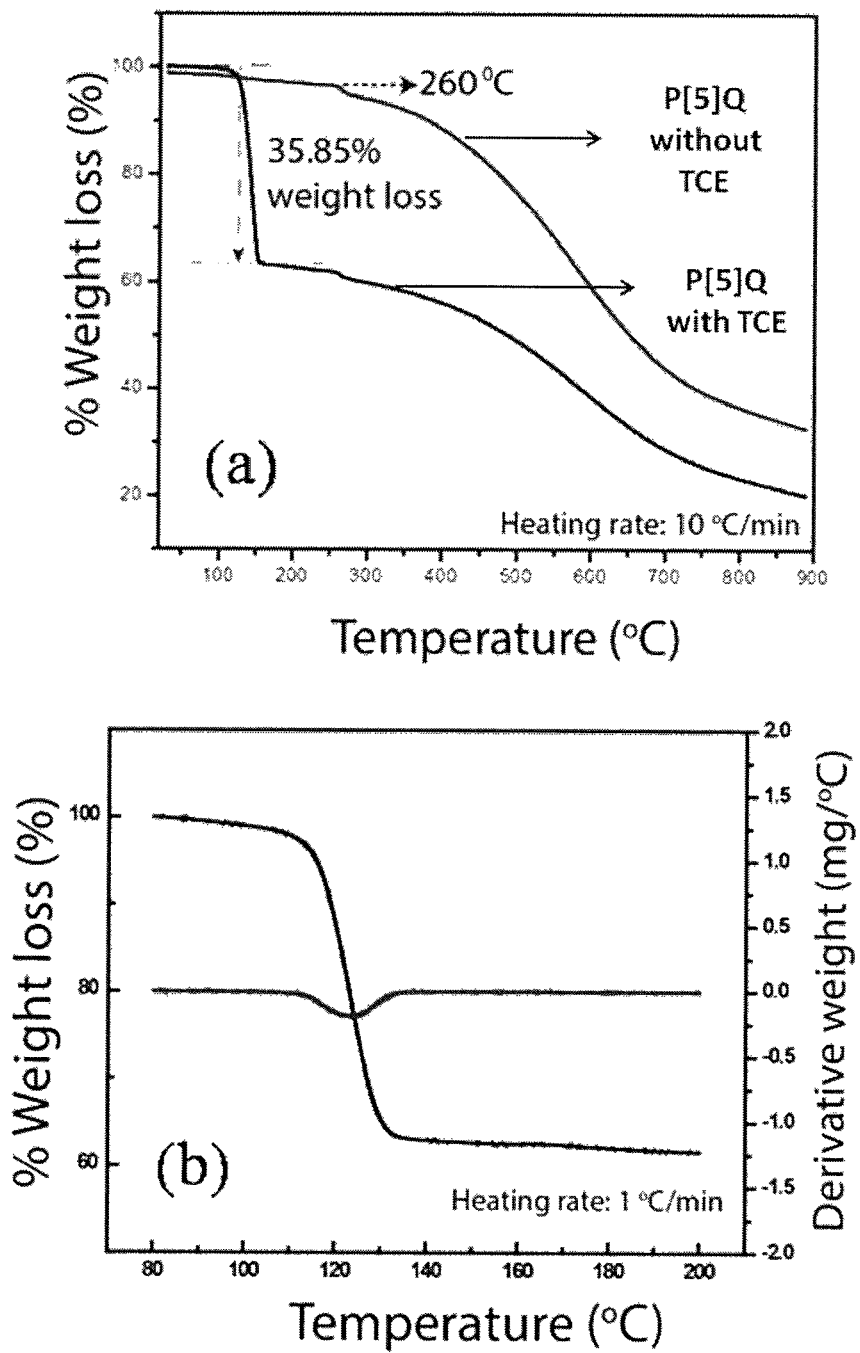

FIGS. 8a and 8b show thermal analysis (FIG. 8a) TGA of P[5]Q with and without TCE obtained at a heating rate of 10° C./min in nitrogen atmosphere; (FIG. 8a), while FIG. 8b shows TGA and DTG of P[5]Q.2TCE performed under the same conditions.

Figure 9:
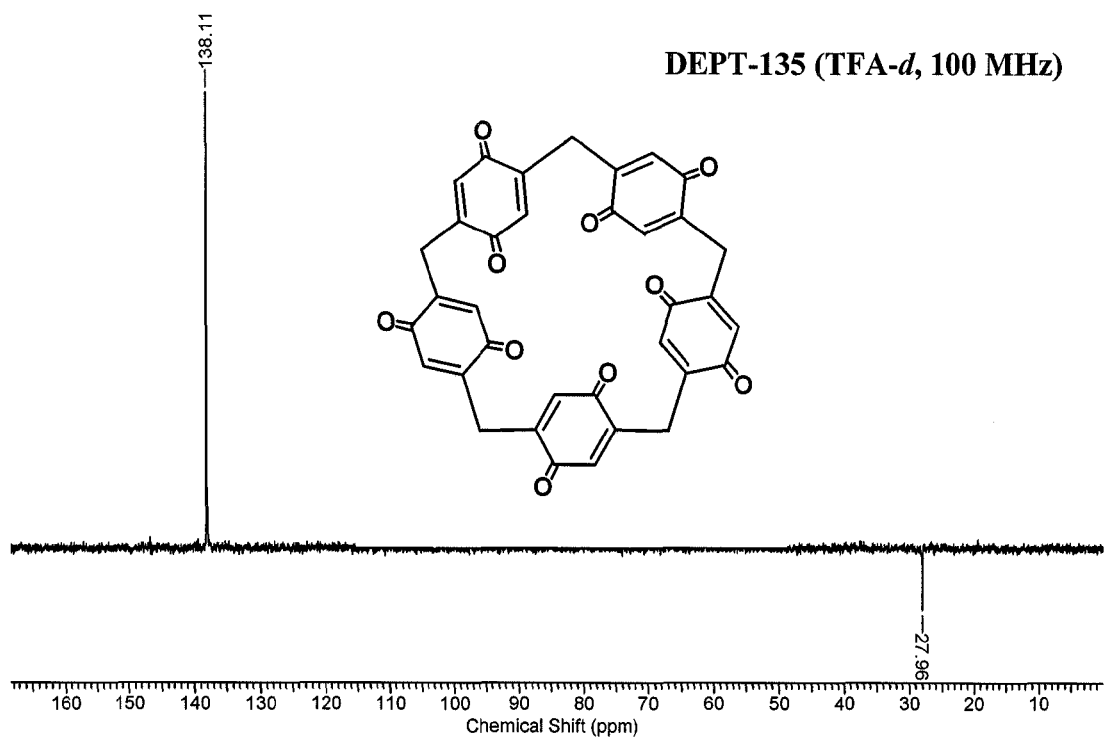

FIG. 9 depicts the DEPT-135 [100 MHz]spectrum of P[5]Q.

Figure 10:
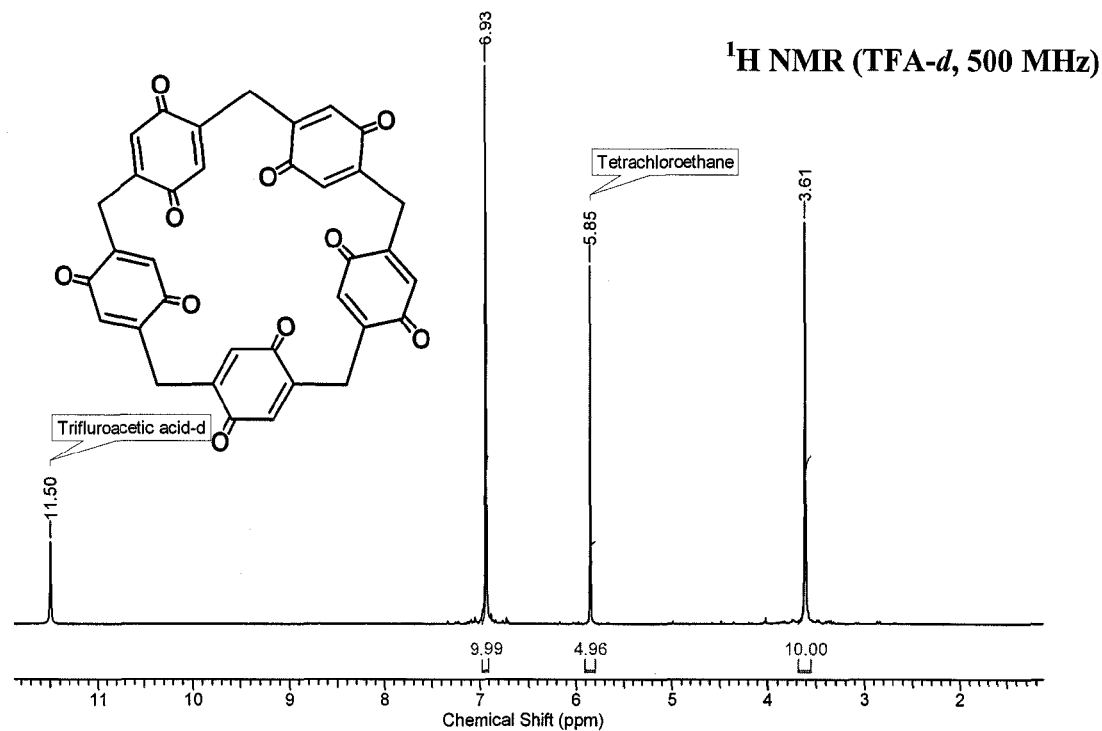

FIG. 10 depicts the $^1$H NMR [500 MHz]spectrum of P[5]Q (Sample from another batch without MeOH wash)

Figure 11:
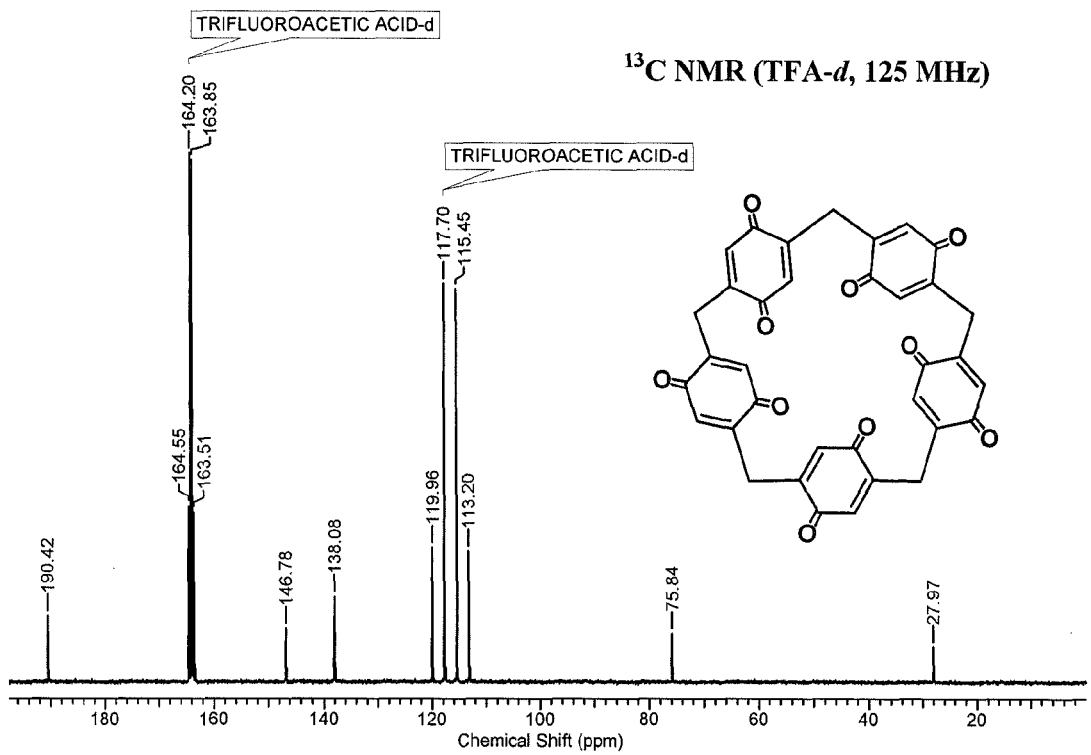

FIG. 11 depicts the $^{13}$C NMR [125 MHz]spectrum of P[5]Q (Sample from another batch without MeOH wash)

Figure 12:
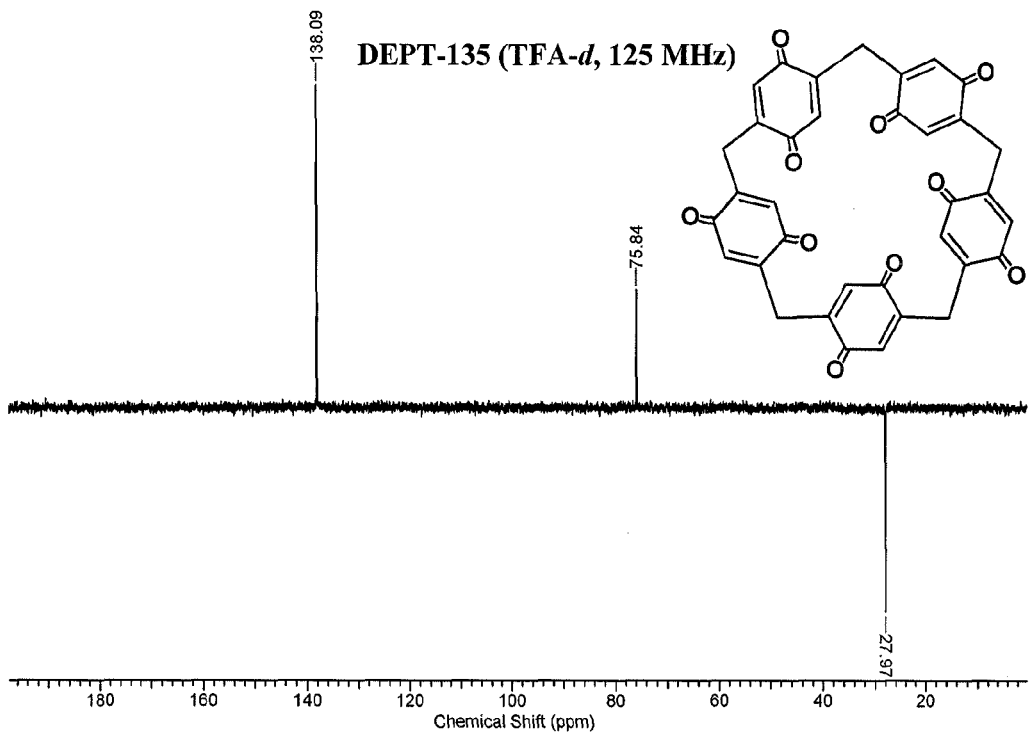

FIG. 12 depicts the DEPT-135 [125 MHz]spectrum of P[5]Q (Sample from another batch without MeOH wash)

Figure 13:
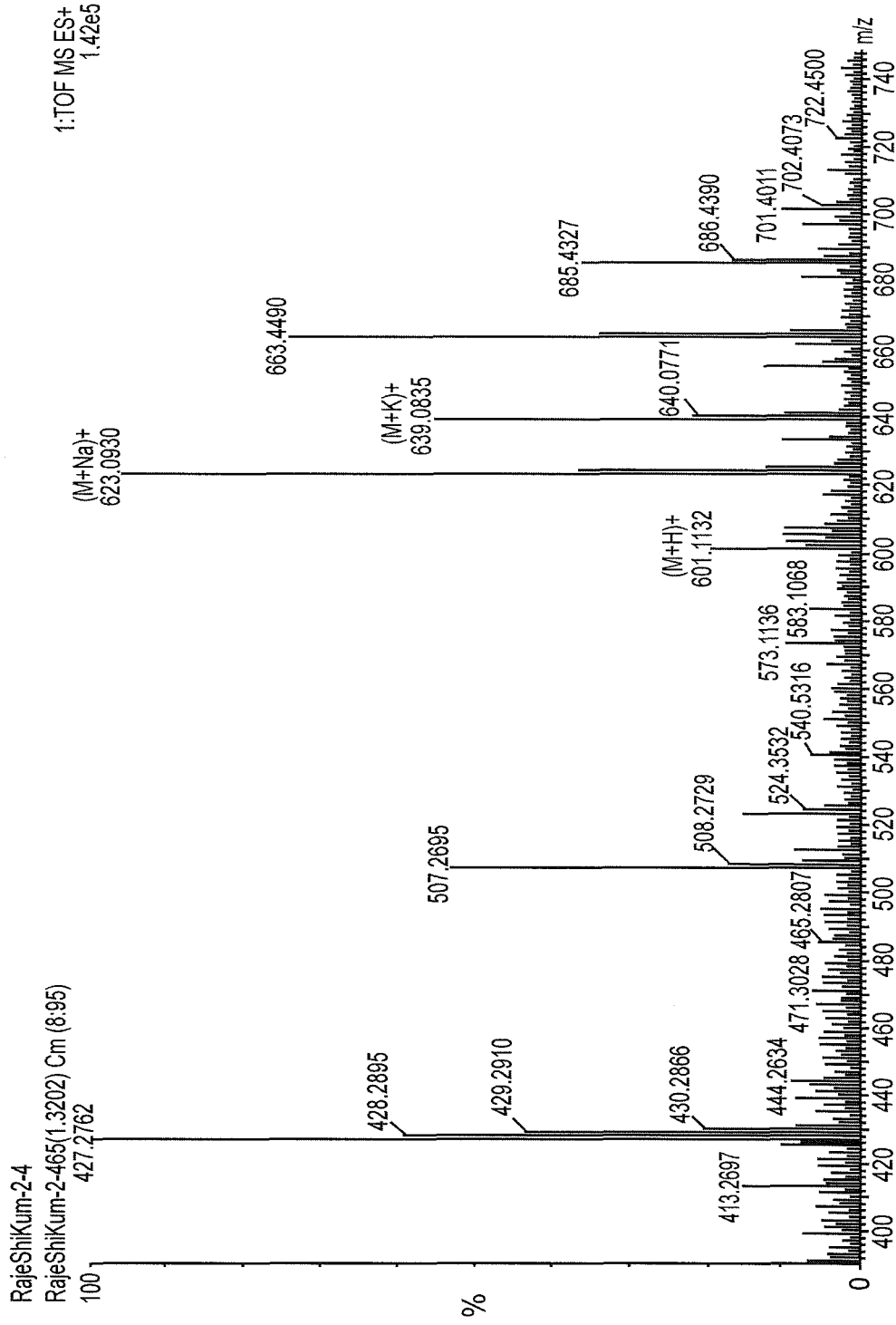

FIG. 13 depicts the Mass spectrum of P[5]Q.

Figure 14:
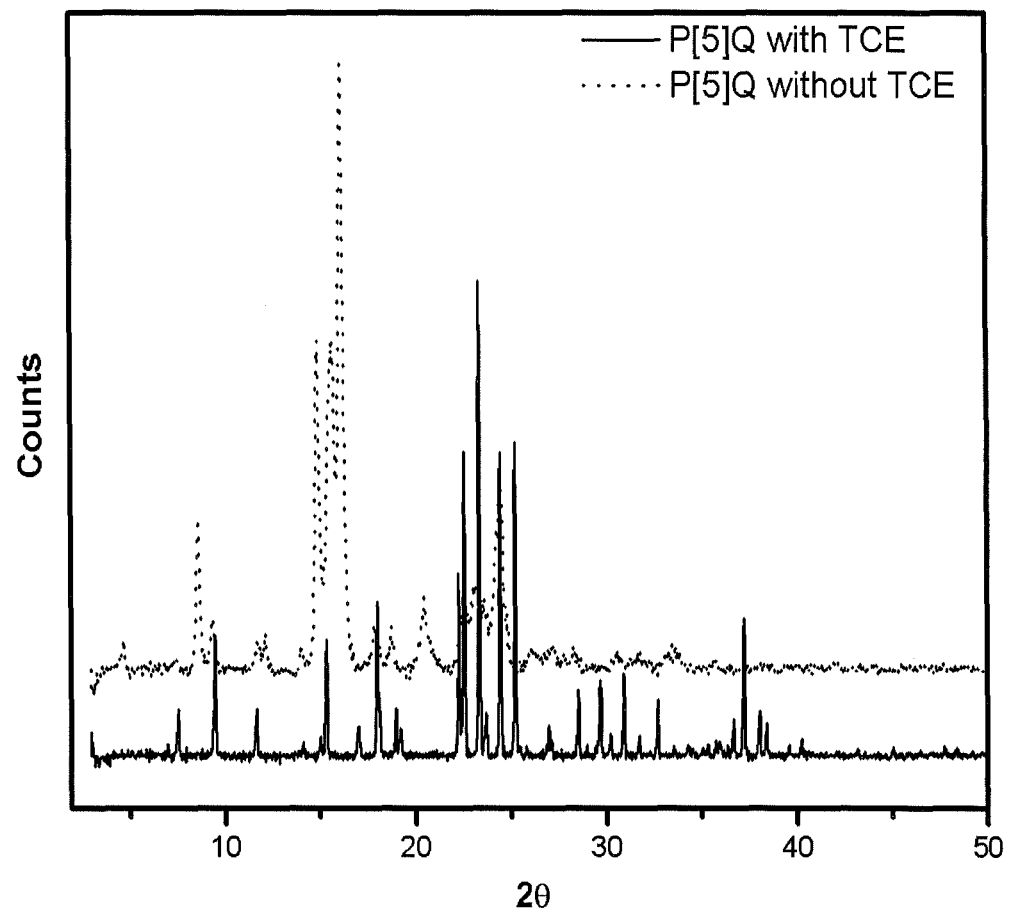

FIG. 14 depicts the powder XRD patterns of P[5]Q with and without associated TCE molecules (pI provide black and white figures)

DETAILED DESCRIPTION OF THE INVENTION

The invention will now be described in detail in connection with certain preferred and optional embodiments, so that various aspects thereof may be more fully understood and appreciated.

The term 'TCE' as used herein refers to '1,1,2,2,-tetrachloroethane'.

The term 'P[5]Q' as used herein refers to 'pillar[5] quinone'.

The present invention provides crystalline form of pillar[5] quinine, optionally containing TCE.

The present invention provides crystalline form of pillar[5] quinone wherein an X-ray powder diffraction (XRPD) pattern contains major peaks at about 3.042, 7.538, 9.486, 11.667, 15.023, 15.358, 16.979, 17.997, 18.952, 22.279, 22.570, 23.363, 23.718, 24.442, 25.243, 28.552, 29.698, 30.916, 32.692, 37.194, 38.036.

The present invention provides crystalline form of pillar[5] quinone wherein an X-ray powder diffraction (XRPD) pattern contains peaks at about 8.61, 14.855, 15.742, 16.16, 20.468, 22.392, 23.173, 24.206, 24.541 in the absence of solvent.

The present invention provides an easy-to-operate and chromatography-free process for the preparation of crystalline pillar[5]quinone in multi-gram quantities by the oxone/ iodobenzene-mediated oxidativede-aromatization of readily available 1,4-dimethoxypillar[5]arenes in good yields.

The present invention provides an efficient, simple and cheaper process for the preparation of pillar[5]quinone optionally containing TCE comprising the steps of:

(a) mixing 1,4-dimethoxypillar[5]arene, acetonitrile, and an oxidizing agent in water to obtain a reaction mixture;
(b) adding iodobenzene to the reaction mixture of step (a) in a mole ratio of 1:2 to obtain a solution; and
(c) stirring the solution of step (b) for a time duration in the range of 45-48 hrs at a temperature in the range of 25-35° C. followed by purification with a solvent.

The solvent used for purification in step (c) is 1,1,2,2,-tetrachloroethane. The oxidizing agent used is oxone ($2KHSO_5.KHSO_4.K_2SO_4$).

The process for the preparation of pillar[5]quinone from 1,4-dimethoxypillar[5]arenes is shown below in Scheme 1:

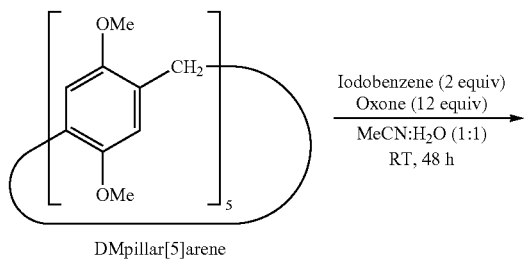

Scheme: 1

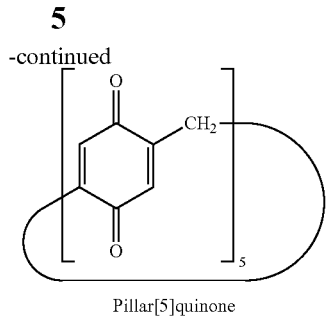

Pillar[5]quinone

The process for the preparation of pillar[5]quinone comprises mixing finely ground 1,4-dimethoxypillar[5]arene, acetonitrile and a solution of oxone (2KHSO$_5$.KHSO$_4$.K$_2$SO$_4$) in water. Addition of iodobenzene to the reaction mixture followed by stirring at room temperature for 48 hrs. The reaction mixture then poured into water and filtered under suction. The yellow colored residue repeatedly washed with plenty of water followed by methanol and dried. Then the crude compound is purified by dissolving the crude compound in boiling 1,1,2,2-tetrachloroethane (TCE) and filtered under suction to remove some undissolved brownish material. The reddish-colored clear filtrate was left at room temperature for 6 hrs and later maintained at 6 to 10° C. for 8 hrs. The microcrystalline mass was filtered under suction, washed with small portions of chilled TCE and methanol, and dried over P$_2$O$_5$, to obtain P[5]Q as a lemon-yellow colored light-weight solid.

EXAMPLES

The following examples are given by way of illustration of the working of the invention in actual practice and should not be construed to limit the scope of the present invention in any way.

Example 1

Synthesis of Pillar[5]Quinone

A single-necked 2 L round bottom flask was charged with finely ground 1,4-dimethoxypillar[5]arene (25.0 g, 33.3 mmol), acetonitrile (350 mL) and a solution of oxone (2KHSOs5.KHSO$_4$.K$_2$SO$_4$, 122.9 g, 400.0 mmol) in water (350 mL). To the above mixture, iodobenzene (7.5 mL, 66.6 mmol) was added. The reaction mixture, after vigorously stirring at room temperature (25° C.) for 48 hours, was poured into water and filtered under suction. The yellow colored residue was repeatedly washed with plenty of water followed by methanol and dried.
Purification Carried Out by the Following Crystallization Procedure The crude compound (18.264 g) was first dissolved in boiling 1,1,2,2-tetrachloroethane (TCE, 350 mL), and filtered under suction to remove some undissolved brownish material (0.813 g), which was discarded. The reddish-colored clear filtrate was left at room temperature (25° C.) for 6 hrs (substantial amount of P[5]Q crystallized out during this period), and later maintained at about 5° C. for 8 h. The microcrystalline mass was filtered under suction, washed with small portions of chilled TCE (3×10 mL) and methanol (3×15 mL), and dried over P$_2$O$_5$, to afford P[5]Q as a lemon-yellow colored light-weight solid (6.66 g, 33%). mp: compound does not melt, but decomposes above 250° C.;

IR (Nujol mull, ν (cm$^{-1}$)): 1654 (m), 1610 (m), 1461 (s), 1377 (s), 1286 (m), 1250 (m), 1125 (m), 921 (m), 722 (m); $^1$H NMR (400 MHz, trifluoroacetic acid-d): δ=6.90 (s, 10H, H$_{quinone}$), 3.58 (s, 10H, CH$_2$). $^{13}$C NMR (100 MHz, trifluoroacetic acid-d): δ=190.5 (CO), 146.8 (C—CH$_2$), 138.1 (C$_{quinone}$), 28.0 (CH$_2$). $^1$H NMR (trifluoroacetic acid-d, 500 MHz, ppm): δ 6.93 (s, 10H, quinone CH), δ 3.61 (s, 10H, methylene protons); $^{13}$C NMR (trifluoroacetic acid-d, 125 MHz, ppm) δ 190.5 (C of carbonyl), δ 146.8 (C of quinone ring attached to methylene group), δ 138.1 (tertiary C of quinone ring), δ 28.0 (methylene C); HRMS (TOF MS ES+): calcd for C$_{35}$H$_{21}$O$_{10}$ (M+H)$^+$: 601.1129, found: 601.1132; calcd for C$_{35}$H$_{20}$O$_{10}$Na (M+Na)$^+$: 623.0949, found: 623.0930.

The TCE filtrate was evaporated under reduced pressure and the reddish residue was triturated with hot methanol (100 mL), and filtered (while hot) and dried to afford an off-white residue which was found to be the starting material (8.371 g). Thus, yield of crystallized Pillar[5]quinone based on recovered starting material is 50%.

Example 2

Surface Characterization of Pillar[5]Quinone

In order to determine the morphology and topography of the Pillar[5]quinone, crystallized from the 1,1,2,2-tetrachloroethane SEM, TEM and AFM were obtained.
SEM
Samples were analyzed on a FEI make SEM system of Quanta 200 3D series (dual beam ESEM) bearing tungsten filament as the electron source operated at 10 kV. The secondary electron image (FIG. 3a) shows cuboidal structures with the length being around 30-50 μm. The sample seems to have uniform morphology throughout. Cuboidal-like structures of Pillar[5]quinone no more remain when TCE is dispossessed (FIG. 4).
TEM
TEM images were recorded using FEI Tecnai G2 F20 X-TWIN TEM at an accelerating voltage of 200 kV. TEM sample was prepared by drop casting the dispersed solution of P[5]Q-TCE in chloroform on a carbon-coated copper grid TEM Window (TED PELLA, INC. 200 mesh). Dispersion of P[5]Q-TCE in chloroform was done by sonicating the solution for two minutes. TEM image (FIG. 3b) reveals the shortened dimensions of the supramolecular rod-like structures. The length and breadth have reduced considerably from few micrometers to ca. 200 nm and 20 nm respectively. This, we believe, is due to the weak non-covalent interactions between TCE and P[5]Q aptly broken by the dispersing solvent interaction and by sonication. Nevertheless, it is evident that 1,1,2,2,-Tetrachloroethane is playing a pivotal role in aggregating the Pillar[5]quinone by tethering them together.
AFM
Atomic Force Microscope (AFM) images of P[5]Q-TCE were obtained by using digital instrument nanoscope-IV, multimode scanning probe microscope at ambient conditions in the tapping mode. Sampling was done by dispersing P[5]Q-TCE in chloroform and drop casting on a silicon substrate. The height of the rod-like structure was determined by cross section analysis. The average height of the rod analyzed from three different zones (FIG. 4) is ca. 90 nm±3 nm. The rod exhibits convex curvature (FIG. 5).
Thermogravimetric Analysis (TGA)
Thermogravimetric analysis (TGA) was conducted to determine the weight loss upon increasing temperature at constant rate. Expectedly, P[5]Q.2TCE showed weight loss of 35.85% against the calculated loss of 35.87% for two TCE molecules, indicating the vaporization of associated TCE molecules. Differential thermogravimetry (DTG) performed at a heating rate of 1° C./min in the range of 80° C.-200° C., showed single minima at 123.7° C., signifying that the energy of association between TCE and P[5]Q is not very significant. (FIG. 8) Nevertheless, helps in formation of extensive self-assembly.

ADVANTAGES OF THE PRESENT INVENTION a. Fabrication of (pseudo) rotaxanes or poly(pseudo)rotaxanes, supramolecular dimers or polymers, artificial transmembrane proton channels, fluorescent sensors and molecular recognizers.
b. Environmentally benign condition.
c. Non chromatographic process.
d. Purification by crystallization.

We claim:

1. A process for the preparation of crystalline form of pillar[5]quinone, wherein said process comprises the following steps:
   (a) mixing 1,4-dimethoxypillar[5]arene, acetonitrile, and an oxidizing agent in water to obtain a reaction mixture;
   (b) adding iodobenzene to the reaction mixture of step (a) in a mole ratio of 1:2 to obtain a solution; and
   (c) stirring the solution of step (b) for a time duration in the range of 45-48 hrs at a temperature in the range of 25-35° C. followed by purification with a solvent to obtain a crystalline form of pillar[5]quinone.

2. The process according to claim 1, wherein the oxidizing agent in step (a) is $2KHSO_5.KHSO_4.K_2SO_4$ (oxone).

3. The process according to claim 1, wherein the solvent used for purification in step (c) is 1,1,2,2,-tetrachloroethane.

4. The process according to claim 1, wherein mole ratio of 1,4-dimethoxypillar[5]arene and oxidizing agent in step (a) is 1:12.

5. The process according to claim 1, wherein yield of pillar[5]quinone is in the range of 32% to 34%.

* * * * *

UNITED STATES PATENT AND TRADEMARK OFFICE
CERTIFICATE OF CORRECTION

| | | |
|---|---|---|
| PATENT NO. | : 9,000,224 B1 | |
| APPLICATION NO. | : 14/445471 | |
| DATED | : April 7, 2015 | |
| INVENTOR(S) | : Jessy Sanjayan Gangadhar | |

It is certified that error appears in the above-identified patent and that said Letters Patent is hereby corrected as shown below:

Title page, item [30] under Foreign Application priority Data:

(30) 2243/DEL/2103  should be  2243/DEL/2013

Signed and Sealed this
Twenty-fifth Day of August, 2015

Michelle K. Lee
*Director of the United States Patent and Trademark Office*